(12) United States Patent
Saleem et al.

(10) Patent No.: US 9,951,343 B2
(45) Date of Patent: Apr. 24, 2018

(54) **PROCESS FOR RECOMBINANT PROTEIN EXPRESSION AUGMENTATION IN *BACILLUS* EXPRESSION SYSTEM**

(71) Applicants: Faiza Saleem, Lahore (PK); Hyun-Woo Park, Riverside, CA (US); Shagufta Naz, Lahore (PK); Abdul Rauf Shakoori, Lahore (PK)

(72) Inventors: Faiza Saleem, Lahore (PK); Hyun-Woo Park, Riverside, CA (US); Shagufta Naz, Lahore (PK); Abdul Rauf Shakoori, Lahore (PK)

( * ) Notice: Subject to any disclaimer, the term of this patent is extended or adjusted under 35 U.S.C. 154(b) by 0 days.

(21) Appl. No.: 14/707,793

(22) Filed: May 8, 2015

(65) Prior Publication Data
US 2017/0183668 A1 Jun. 29, 2017

(51) Int. Cl.
*C12P 21/02* (2006.01)
*C12N 15/75* (2006.01)
*C12N 15/90* (2006.01)
*C07K 14/325* (2006.01)
*C07K 14/32* (2006.01)
*C12N 15/67* (2006.01)

(52) U.S. Cl.
CPC .............. *C12N 15/75* (2013.01); *C07K 14/32* (2013.01); *C07K 14/325* (2013.01); *C12N 15/67* (2013.01); *C12N 15/902* (2013.01)

(58) Field of Classification Search
None
See application file for complete search history.

(56) References Cited

PUBLICATIONS

Salis et al. (2009) Nature Biotechnology vol. 27, pp. 946-950. (Year: 2009).*

* cited by examiner

*Primary Examiner* — James S Ketter
(74) *Attorney, Agent, or Firm* — Sarfaraz K. Niazi

(57) ABSTRACT

A process for efficient expression of a foreign gene in a *Bacillus* host was developed by varying the length and nucleotide sequence in the spacer region between ribosomal binding sequence (RBS) and initiation codon (ATG) of the gene. *Bacillus thuringiensis* cry2Ac gene was selected as a model gene because it requires an upstream open reading frame designated as orf2 for its efficient expression and crystallization in a *Bacillus* host.

3 Claims, 2 Drawing Sheets

PROCESS FOR RECOMBINANT PROTEIN EXPRESSION AUGMENTATION IN *BACILLUS* EXPRESSION SYSTEM

BACKGROUND OF THE INVENTION

The most important barrier for efficient expression of foreign or native genes in any organism many times resides at the level of mRNA translation. As stability of mRNA is a major determinant of gene expression. According to the canonical model, the main signal for the ribosome to land on mRNA and start protein synthesis is the Shine-Dalgarno sequence, a purine-rich region located upstream of the start codon and complementary to the 3'-terminal sequence AUCACCUCCUUA (SEQ ID NO 1) (antiSD) of the 16S rRNA is thought that the SD-antiSD interaction directs the initiation codon to the P site of the 30S subunit at the first step of translation initiation, and that the efficiency of initiation and, eventually, of overall translation depends on the degree of complementarity of the two sequences: the tighter the SD duplex is, the more stable is the initiation complex and the higher the level of translation.

The 5' untranslated region (5' UTR) (also known as a Leader Sequence or Leader RNA) is the region of an mRNA that is directly upstream from the initiation codon. This region is important for the regulation of translation of a transcript by differing mechanisms in viruses, prokaryotes and eukaryotes. While called untranslated, the 5' UTR or a portion of it is sometimes translated into a protein product. This product can then regulate the translation of the main coding sequence of the mRNA.

In many other organisms, however, the 5' UTR is completely untranslated, instead forming complex secondary structure to regulate translation. The 5' UTR has been found to interact with proteins relating to metabolism and proteins translate sequences within the 5' UTR. In addition, this region has been involved in transcription regulation, such as the sex-lethal gene in Drosophila. The 5' UTR begins at the transcription start site and ends one nucleotide (nt) before the initiation codon (usually AUG) of the coding region. In prokaryotes, the length of the 5' UTR tends to be 3-10 nucleotides long while in eukaryotes it tends to be anywhere from 100 to several thousands nucleotides long. For example, the ste11 transcript in *Schizosaccharomyces pombe* has a 2273 nucleotide 5' UTR while the lac operon in *Escherichia coli* only has 7 nucleotides in its 5' UTR The differing sizes are likely due to the complexity of the eukaryotic regulation which the 5' UTR holds, as well as the larger preinitiation complex which must form to begin translation.

The prokaryotic 5' UTR contains a ribosome binding site (RBS), also known as the Shine Dalgarno sequence (AGGAGGU) which is usually 3-10 base pairs upstream from the initiation codon. As the 5' UTR has a high GC content, secondary structures often occur within it. Hairpin loops are one such secondary structure that can be located within the 5' UTR. These secondary structures also impact the regulation of translation. In prokaryotes, the initiation of translation occurs when IF-3 along with the 30S ribosomal subunit bind to the Shine-Dalgarno sequence of the 5' UTR. This then recruits many other proteins that such as the 50S ribosomal subunit that allows for translation to begin.

Each of these steps regulates the initiation of translation. Translation machineries of *Bacillus* species are quite specific and require homologous ribosome binding sites RBS. The RBS usually contains a sequence GGAGG. It has an average free energy for binding is about −17 kcal/mol at 3'end of the 16S ribosomal RNA. Supplying an efficient *Bacillus* RBS sequence to the gene of interest is one solution, but it does not always work because the secondary structure around the translation initiation site also plays a pivotal role in determining translation efficiency. The sequence GGAGG in the RBS is usually highly conserved; and the spacer region between the GGAGG sequence and initiation codon is approximately eight bases long and rich in A and U nucleotides.

The absence of G and C residues around the RBS is thought to be optimal for ribosome binding. The crystals produced by *Bacillus thuringiensis* (Bt) mainly consist of Cry proteins, most of which are toxic for specific insects and consequently *B. thuringiensis* has been widely and successfully used as a biopesticides for more than 50 years. The crystal inclusion can account for up to 25% of the dry weight of *B. thuringiensis* cells. The mechanism for the massive expression of Cry proteins in *B. thuringiensis* has been investigated and involves numerous factors: transcriptional regulation, cry gene copy number, the stability of cry gene mRNA, and the accumulation and crystallization of Cry proteins.

Structure-based protein engineering of Cry toxins may direct the search for variants with broader susceptible species spectra, optimal potency, and stability properties. Cry2Aa is among an unusual subset of Cry proteins possessing broad insect species specificity by exhibiting high specific activity against two insect orders, Lepidoptera and Diptera. It is lethal to more lepidopteran species than the Cry1 toxins deployed against agriculturally important Lepidoptera and exhibits a low level of cross resistance in Cry1A-resistant insects. Also, the mode of action of Cry2Aa may be distinct from that of other Cry toxins. Thus, it could serve as a platform for the design of Cry toxins with broader susceptible species spectra and minimal Cry1A-derived cross resistance in the field.

Cry2A protein is of smaller mass having no C-terminal crystallization domain like that in the 130-140 kDa Cry proteins (e.g Cry1). The massive accumulation or crystallization of these Cry proteins generally requires the presence of additional proteins encoded by genes in the same operon. Additional protein of small size (29 kDa), have no insect toxicity and are not the main components of the crystals; rather, it enhances the accumulation or crystallization of their accompanying Cry protein. Consequently, it is described as an accessory proteins or helper protein. Helper protein is encoded by the orf1 and orf2 genes in the cry2A operon. Orf2 is necessary for the crystallization of Cry2A. It contains 11 tandem repeats of a 15/16 amino acid motif that is acidic in nature. Orf2 and Cry2A can be co-precipitated, evidence of interaction between the two proteins Indeed, Orf2 serves as a crystallization factor by interacting with the Cry2A protein, possibly acting as a template or scaffold.

To further investigate the role of Orf1 and Orf2 in Cry2A synthesis for potential applied use, we studied the effects of expressing cry2A alone or together with orf1 and orf2 by using the bioinformatics approach and experimental assessment. In this study, cyt1A promoter combined with the STAB-SD sequence (cyt1A-p/STAB-SD) was used as chimeric cyt1A-p/STAB-SD expression system has been shown to significantly improve synthesis of several Cry proteins and Bin toxins. Furthermore, the length and composition of the spacer region (RBS-ATG) was varied to scrutinize its effect on efficient production of Cry2Ac.

BRIEF SUMMARY OF THE INVENTION

A novel process for efficient expression of foreign gene in *Bacillus* host was developed by varying the length and nucleotide sequence in the spacer region between ribosomal binding sequence (RBS) and initiation codon (ATG) of the gene. Bacillus thuringiensis cry2Ac gene was selected as a model gene since it requires an upstream open reading frame designated as orf2 for its efficient expression and crystallization in Bacillus host. The ORF2 acts as chaperone and provides a nucleation centre for growing crystals of Cry2Ac. The role of ribosomal binding sequence (RBS) and spacer region (RBS-ATG) was analyzed in Cry2A expression without helper protein in Bacillus expression host.

Mutation in the RBS and spacer region were introduced by changing length and composition of naturally existing sequence. Bacillus thuringiensis cry2Ac gene was selected as a model gene that was expressed in acrystalliferous strain 4Q7 of the same species. Insecticidal crystal (Cry) toxins from Bacillus thuringiensis (Bt) are widely employed for biological control of pest insects through Bt formulations as well as transgenic plants. Cry2Ac has dual toxicity against lepidopteran as well as dipteran insects. cry2Ac gene appears as a third gene in an operon that consists of three open reading frames (orfs). In order to enhance activity of Cry2Ac toxin from HD29 strain of Bacillus thuringiensis subsp. galleriae (Bacillus Genetic Stock Center ID 4G5; Serotype 5a5b), gene was over-expressed in acrystalliferous Bt strain 4Q7. The number as well as sequence of nucleotides between ribosomal binding site (RBS) and initiation codon (ATG) were altered in various constructs and were cloned in pSTAB shuttle expression vector containing the cyt1A promoter from B. thuringiensis subsp. israelensis combined with the STAB-SD sequence from B. thuringiensis subsp. morrisoni strain tenebrionis. The resulting plasmid was introduced in 4Q7, an acrystalliferous mutant strain of B. thuringiensis subsp. israelensis. Expression of cry2Ac varied greatly in all transformants, and was significantly enhanced in mutants having additional ATG in the spacer region. A maximum vigor of about 10 times was observed in pPFS-2Ac11 construct which also produced parasporal inclusions unlike wildtype Cry2Ac.

DETAILED DESCRIPTION OF THE INVENTION

Figure 1:
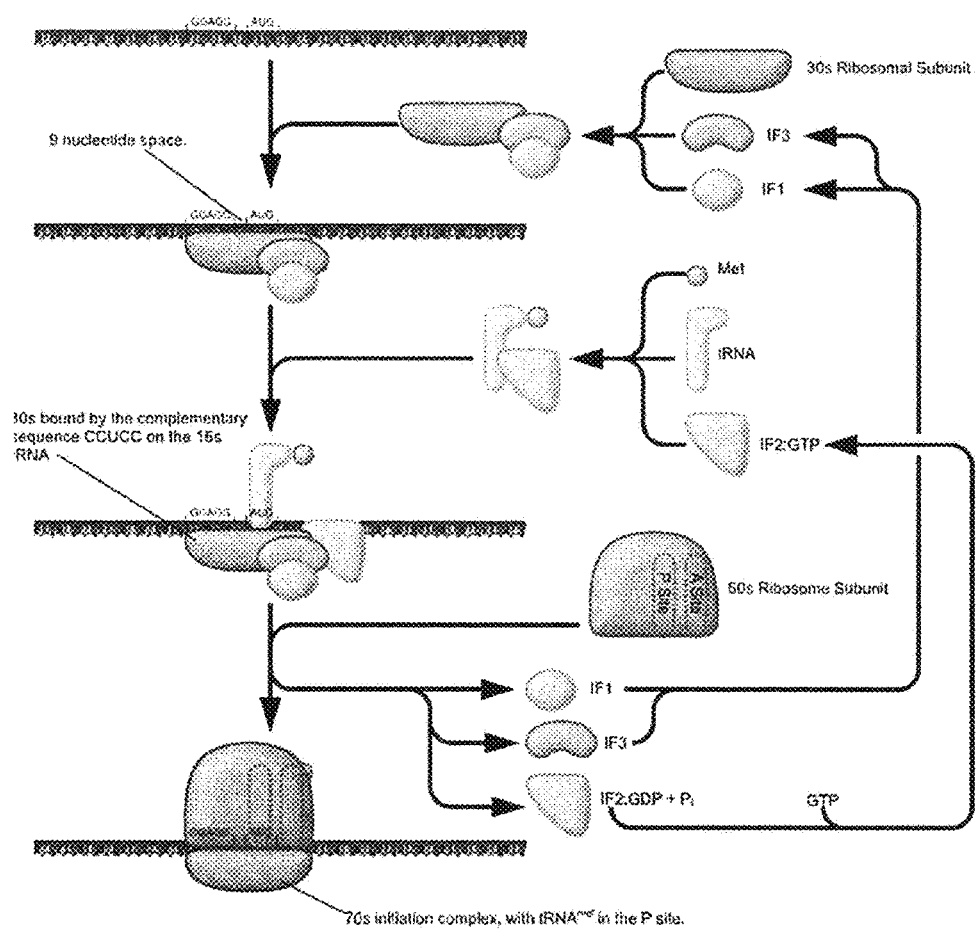
FIG. 1 depicts a protein synthesis in a prokaryotic system.
Figure 2:
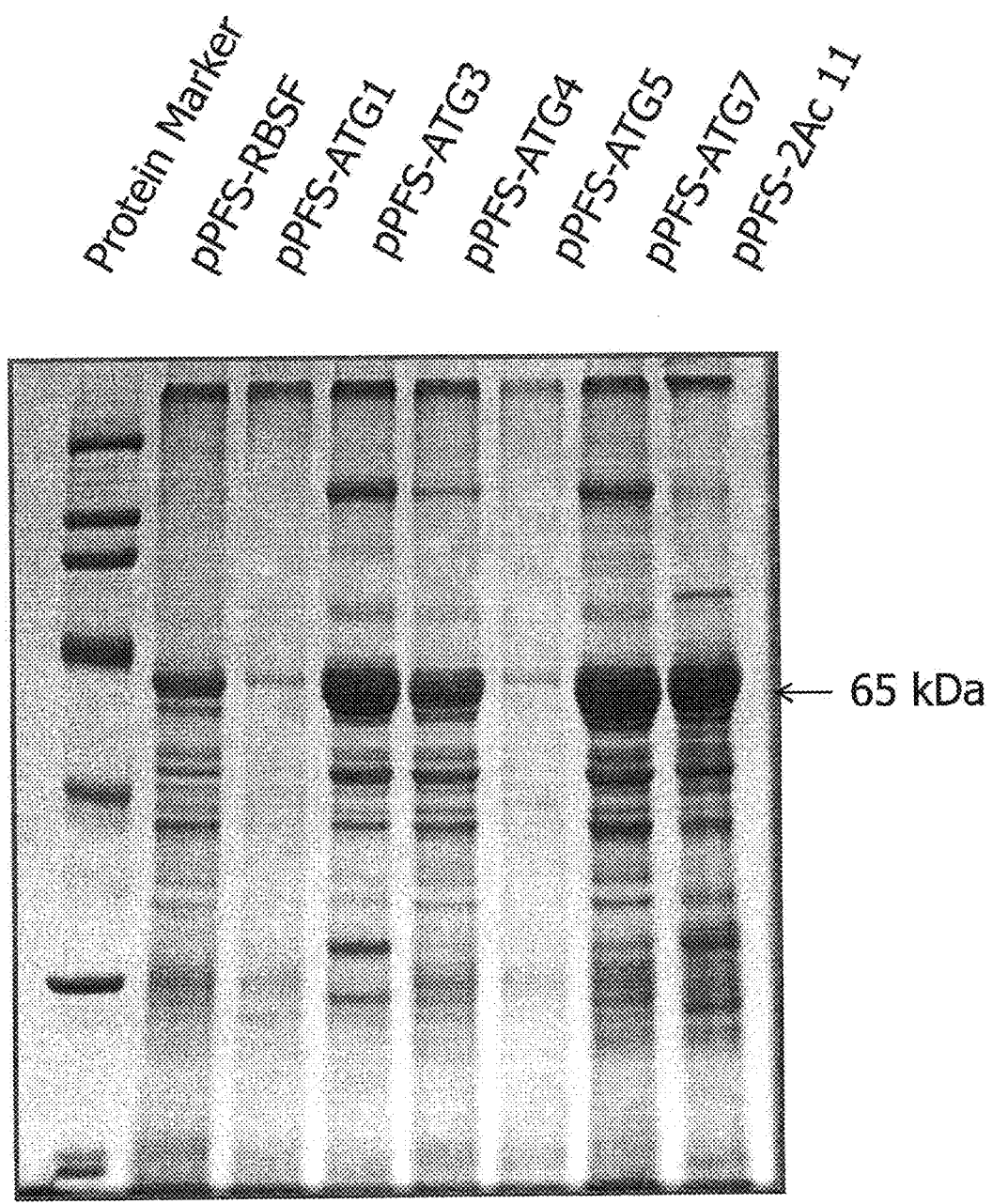
FIG. 2 depicts SDS-PAGE analysis of Cry2Ac mutants in the absence of both Orf1 and Orf2 under cyt1A promoter system (pSTAB).

The entire 4.2-kb cry2Ac11 operon from HD29 was amplified by PCR and cloned in pSTAB shuttle expression vector containing the cyt1A promoters from B. thuringiensis subsp. israelensis combined with the STAB-SD sequence from B. thuringiensis subsp. morrisoni strain tenebrionis. The resulting plasmid was introduced in 4Q7, an acrystalliferous mutant strain of B. thuringiensis subsp. israelensis. Furthermore, Cry2Ac was produced in 4Q7 in the absence of both orf1 and orf2. Cultures, grown on nutrient agar overnight, were observed under phase-contrast microscope.

For analysis of protein contents of each construct, 500 µl of overnight cultures, grown in Pre-culture medium, were inoculated in 50 ml of NBG medium supplemented with 25 µg/ml erythromycin and grown at 30° C. for five days with vigorous shaking. Equal volume of each sample was run on 10% SDS-PAGE.

Further some mutations were introduced between RBS and ATG of the gene. The nucleotide sequence as well as number was altered in the spacer region as shown in Table 1. This was achieved by amplifying promoter and gene independently with primers having extra bases and then co-ligated them in pSTAB and transferred in 4Q7 strain of B. thuringiensis. The expressed protein was analyzed using SDS-PAGE while parasporal crystals were analyzed under phase contrast microscope.

TABLE 1

N-terminal sequence of cry2Ac11 cloned in pHT3101 shuttle vector and expressed in 4Q7 strain of B. thuringiensis

| Sr. No. | Mutated construct | Sequence between RBS and ATG (5'→3') | Expression in 4Q7 Inclusions | SDS-PAGE |
|---|---|---|---|---|
| 1. | pPFS-2Ac11 | GGAGGaattttatATGGTCGACatgaatactgtattg (SEQ ID NO 2) | Yes | +++ |
| 2. | pPFS-ATG1 | GGAGGaattttatATGGTCGACatgaatactgtattg (SEQ ID NO 3) | No | – |
| 3. | pPFS-ATG3 | GGAGGaattttatATG---GACatgaatactgtattg (SEQ ID NO 4) | No | +++ |
| 4. | pPFS-ATG4 | GGAGGaattttatATGGTC---atgaatactgattg (SEQ ID NO 5) | No | ++ |
| 5. | pPFS-ATG5 | GGAGGaattttatATGGTCGAC---aatactgtattg (SEQ ID NO 6) | No | – |
| 6. | pPFS-ATG7 | GGAGGaattttatATG------atgaatactgtattg (SEQ ID NO 7) | No | +++ |

TABLE 1-continued

N-terminal sequence of cry2Ac11 cloned in pHT3101 shuttle vector and expressed in 4Q7 strain of *B. thuringiensis*

| Sr. No. | Mutated construct | Sequence between RBS and ATG (5'→3') | Expression in 4Q7 Inclusions | SDS-PAGE |
|---|---|---|---|---|
| 7. | pPFS-Orf3 | GGAGGaattttat---------atgaatactgtattg (SEQ ID NO 8) | No | |

RNA was extracted from 14 hrs old cultures using Trizol reagent and used in Quantitative PCR to determine mRNA level of cry2Ac gene using real time PCR.

RESULTS

We investigated the quantitative relationship between stability of the secondary structure in 5' translated region and protein expression levels in Bt. we systematically introduced random mutation in RNA hairpins along the translation initiation region starting from the RBS of mRNA up to the beginning of the coding region (RBS-ATG).

Previous results suggested that mRNA stability is dependent on the level of its translation. The smaller and more negative ΔG which is the free energy difference between folded and unfolded states, the more stable is the hairpin structure. Although the stability of the secondary structure around the SD sequence has been shown to be inversely related to expression level. High instability of this region provides only the accessibility of the ribosome was thought to play a key role in translation in bioinformatics tools. Although these two approaches differ to some extent, the predictive value of both models is similar, since the same key factors (the secondary structure around the start codon and the ribosome binding affinity) are taken as determining translation efficiency.

Despite the considerable values of these models, expression of wild ORF3 is low as this may be due to other steps of translation which act as limiting factor. Another reason behind this is that we express wild ORF3 without ORF2 under natural condition as it was studied by the literature that ORF2 duplication unit for Cry2Aa may provide attachment (matrix) or scaffold (scaffold) to the formation of crystals and can also help misfolded protein crystals refold into the right structure to immunize it to the risk of degradation, so as to enhance the protein crystal structure and stability. That's why wild ORF3 unit for Cry2Aa showed the lowest expression level.

The 29-kDa protein encoded as the Orf2 of the Cry2Ac11 operon acts like a chaperone, assisting Cry2Ac crystallization in acrystalliferous *B. thuringiensis* host. The same function of Orf2 from Cry2Aa operon has been reported. Cyt-P has been reported to enhance net synthesis of Cry4A and Cry11A in *E. coli* and *B. thuringiensis*, as well as Cyt1A production and crystal formation in *B. thuringiensis*. All of the above studies demonstrated that the effect of the 20-kDa on the Cry or Cyt protein synthesis is significant.

Operon and Orf2+Orf3 constructs produced adequate level of toxin. Cry2Ac Operon expressed Cry2Ac11 in the form of big crystals. Constructs lacking Orf2 did not produce any crystals when introduced in 4Q7 strain of *B. thuringiensis*.

ATG3, ATG4, ATG7 and 2Ac11 constructs produced higher level of toxin as compared to the wild type. None of them could produce parasporal inclusions in absence of Orf2 except for 2Ac11 construct that could produce parasporal inclusions visible under phase contrast microscope.

Although ATG3, ATG4, ATG5 and ATG7 showed almost equal messenger levels, but ATG5 failed to make higher concentration of Cry2Ac, whereas only 2Ac11 could produce parasporal inclusion bodies that showed the highest messenger level.

In the present invention, we tried to express Cry2Ac11 operon under Cyt-P promoter in absence of Orf1 as well as Orf2. Our principal findings are the following:
 a. When Cry2Ac11 was expressed in the absence of Orf1 and Orf2, though under strong promoter system (pSTAB), overall yield of the protein was about five times less as compared to when co-expressed with Orf2 or entire operon.
 b. Expression level of cry2Ac has been enhanced up to 10 times by alteration in number and sequence of nucleotides between RBS and ATG.
 c. Sequence of nucleotides between RBS and ATG is critical for expression enhancement.
 d. qPCR revealed similar mRNA level in ATG3, ATG4, ATG5 and ATG7 constructs while the highest was exhibited by 2Ac11 construct.
 e. Addition of an ATG in the spacer region (RBS-ATG) augmented the protein expression many folds in ATG3, ATG4, ATG7 and 2Ac11 constructs.
 f. Only pPFS-2Ac11 produced parasporal inclusions indicating its highest stability.

Bioinformatics Approaches

Salis et al. (2009) developed a mathematical model, called the RBS calculator, to compute the RBS strength. This model considers the energies involved in rRNA-mRNA interaction, mRNA folding, tRNA binding, and the energetic cost of sub-optimal spacing between the RBS and the start codon. This computational tool was proved effective in designing RBS sequences to control relative protein levels.

TABLE 2

Translational efficiency of the mutant constructs as calculated using various softwares

| Sr. No. | Mutated construct | mFOLD ΔG (kcal/mol) | RBS calculator | | | RBS designer: Translational Efficiency |
|---|---|---|---|---|---|---|
| | | | Translation initiation rate | Start codon and position | Accuracy | |
| 1. | pPFS-2Ac11/4Q7 | −0.17 | 58437.4 | ATG (13) | NEQ | 0.28 |
| 2. | pPFS-ATG1/4Q7 | −0.50 | 55104.2 | TTG (14) | not OK | 0.052 |
| 3. | pPFS-ATG3/4Q7 | 2.50 | 73184.1 | ATG (13) | Ok | 0.29 |
| 4. | pPFS-ATG4/4Q7 | 2.20 | 35619.97 | ATG (13) | Ok | 0.031 |
| 5. | pPFS-ATG5/4Q7 | 2.20 | 35619.97 | ATG (13) | Ok | 0.14 |
| 6. | pPFS-ATG7/4Q7 | 1.70 | 143745.7 | ATG (13) | Ok | 0.291 |
| 7. | pPFS-ORF3/4Q7 | 3.10 | 14374 | ATG (13) | Ok | 0.291 |

What is claimed is:

1. A method for high level expression of a heterologous foreign gene in *Bacillus* expression system comprising adding a nucleotide sequence of ATGGTCGACATG (positions 14-25 of SEQ ID NO:4) in the spacer region between ribosomal binding sequence (RBS) and initiation codon (ATG) of the gene and optionally including an ATG in the spacer region.

2. The method of claim 1, wherein the foreign gene is insecticidal crystal toxin gene cry2Ac11.

3. The method of claim 1, wherein expression of crystal toxin is increased by a factor of 2-20 compared to expression without adding the nucleotide sequence in the spacer region.

* * * * *

SEQUENCE LISTING

<160> NUMBER OF SEQ ID NOS: 10

<210> SEQ ID NO 1
<211> LENGTH: 12
<212> TYPE: RNA
<213> ORGANISM: Artificial Sequence
<220> FEATURE:
<223> OTHER INFORMATION: Anti-Shine Delgarno Sequence

<400> SEQUENCE: 1
aucaccuccu ua                                                          12

<210> SEQ ID NO 2
<211> LENGTH: 7
<212> TYPE: RNA
<213> ORGANISM: Artificial Sequence
<220> FEATURE:
<223> OTHER INFORMATION: Prokaryotic Shine Delgarno Sequence

<400> SEQUENCE: 2 aggaggu                                                                 7

<210> SEQ ID NO 3
<211> LENGTH: 5
<212> TYPE: RNA
<213> ORGANISM: Artificial Sequence
<220> FEATURE:
<223> OTHER INFORMATION: Prokaryotic Ribosome Binding Site

<400> SEQUENCE: 3 ggagg                                                                   5

<210> SEQ ID NO 4
<211> LENGTH: 37
<212> TYPE: DNA
<213> ORGANISM: Artificial Sequence
<220> FEATURE:
<223> OTHER INFORMATION: Plasmid Construct pPFS-2Ac11 - sequence between
      RBS and ATG

<400> SEQUENCE: 4
ggaggaattt tatatggtcg acatgaatac tgtattg                                37

<210> SEQ ID NO 5
<211> LENGTH: 37
<212> TYPE: DNA
<213> ORGANISM: Artificial Sequence
<220> FEATURE:
<223> OTHER INFORMATION: Plasmid Construct pPFS-ATG1 - sequence between -continued RBS and ATG

<400> SEQUENCE: 5
ggaggaattt tatattgtcg acatgaatac tgtattg            37

<210> SEQ ID NO 6
<211> LENGTH: 34
<212> TYPE: DNA
<213> ORGANISM: Artificial Sequence
<220> FEATURE:
<223> OTHER INFORMATION: Plasmid Construct - pPFS-ATG3 - sequence
      between the RBS and ATG

<400> SEQUENCE: 6
ggaggaattt tatatggaca tgaatactgt attg            34

<210> SEQ ID NO 7
<211> LENGTH: 34
<212> TYPE: DNA
<213> ORGANISM: Artificial Sequence
<220> FEATURE:
<223> OTHER INFORMATION: Plasmid Construct pPFS-ATG4 - Sequence between
      the RBS and ATG

<400> SEQUENCE: 7
ggaggaattt tatatggtca tgaatactgt attg            34

<210> SEQ ID NO 8
<211> LENGTH: 34
<212> TYPE: DNA
<213> ORGANISM: Artificial Sequence
<220> FEATURE:
<223> OTHER INFORMATION: Plasmid Construct pPFS-ATG5 - Sequence between
      the RBS and ATG

<400> SEQUENCE: 8
ggaggaattt tatatggtcg acaatactgt attg            34

<210> SEQ ID NO 9
<211> LENGTH: 31
<212> TYPE: DNA
<213> ORGANISM: Artificial Sequence
<220> FEATURE:
<223> OTHER INFORMATION: Plasmid Construct pPFS-ATG7 - Sequence between
      the RBS and ATG

<400> SEQUENCE: 9
ggaggaattt tatatgatga atactgtatt g            31

<210> SEQ ID NO 10
<211> LENGTH: 28
<212> TYPE: DNA
<213> ORGANISM: Artificial Sequence
<220> FEATURE:
<223> OTHER INFORMATION: Plasmid Construct pPFS- ORF3 - Sequence between
      the RBS and ATG

<400> SEQUENCE: 10
ggaggaattt tatatgaata ctgtattg            28